United States Patent [19]
Bryant et al.

[11] Patent Number: 6,156,761
[45] Date of Patent: Dec. 5, 2000

[54] SUBSTITUTED TETRALONE DERIVATIVES FOR ENHANCING COGNITION

[75] Inventors: Helen Jane Bryant, Roydon; Mark Stuart Chambers, Puckeridge; Sarah Christine Hobbs, Great Dunmow, all of United Kingdom

[73] Assignee: Merck Sharpe & Dohme Limited, Hoddesdon, United Kingdom

[21] Appl. No.: 09/296,847

[22] Filed: Apr. 22, 1999

[30] Foreign Application Priority Data

Apr. 23, 1998 [GB] United Kingdom ............ 9808667

[51] Int. Cl.⁷ .............. C07D 213/46; C07D 213/50; A61K 31/4418
[52] U.S. Cl. ............. 514/277; 514/278; 514/336; 546/15; 546/280.4; 546/284.4; 546/339
[58] Field of Search ............... 546/15, 280.4, 546/284.4, 339; 514/277, 278, 336

[56] References Cited

U.S. PATENT DOCUMENTS 6,048,877  4/2000  Ahmad et al. .................. 514/319

FOREIGN PATENT DOCUMENTS

WO 9616954  6/1996  WIPO .

OTHER PUBLICATIONS

Damasio, Alzheimer's Disease and related Dementias, Cecil Textbook of Medicine, 20th Edition, vol. 2, pp. 1992–1996, 1996.
Van Rhee, et al., J. Med. Chem., 39: 398–406 (1996).

*Primary Examiner*—Mukund J. Shah
*Assistant Examiner*—Deepak R. Rao
*Attorney, Agent, or Firm*—Shu M. Lee; David L. Rose

[57] ABSTRACT

The present invention provides a compound of formula (I) or a pharmaceutically acceptable salt thereof:

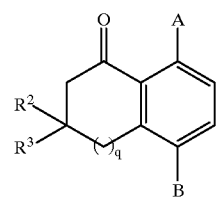

(I)

wherein A, B, R2, R3 and q are as defined in the disclosure, pharmaceutical compositions containing them; methods for their production; their use in therapy and methods of treatment of disease states where cognition enhancement is required, such as Alzheimer's disease.

5 Claims, No Drawings

SUBSTITUTED TETRALONE DERIVATIVES FOR ENHANCING COGNITION

The present invention relates to pharmaceutical compounds which are substituted tetralone derivatives and to their use in therapy. More particularly, this invention is concerned with substituted tetralone derivatives which are ligands for $GABA_A$ receptors, in particular for $GABA_A$ α5 receptors and are therefore useful in therapy particularly where cognition enhancement is required.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, a δsubunit also exists, but is apparently uncommon in the native receptor.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of $GABA_A$ receptors in the rat. Subtype assemblies containing α2 and α3 subunits respectively account for about 25% and 17% of $GABA_A$ receptors in the rat. Subtype assemblies containing an α5 subunit are primarily hippocampal and represent about 4% of receptors in the rat.

A characteristic property of some $GABA_A$ receptors is the presence of a number of modulatory sites, of which the most explored is the benzodiazepine (BZ) binding site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with β2 and γ2. This is the most abundant $GABA_A$ receptor subtype, representing almost half of all $GABA_A$ receptors in the brain.

Two other major populations are the α2βγ2 and α3βγ2/3 subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the $GABA_A$ α5 receptor subtype.

WO-A-9616954 mentions three thienylcyclohexanone derivatives substituted by substituted arylaminocarbonyl on the thiophene ring as fungicides.

Van Rhee et al, *J. Med. Chem.*, 1996, 39, 398–406 discloses related compounds as adenosine receptor antagonists which differ in having an ester group on the thiophene ring.

The present invention provides a compound of formula (I) or a pharmaceutically acceptable salt thereof:

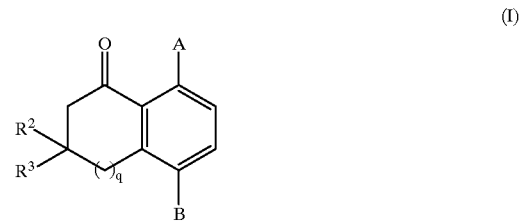

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_p(CH_2)_nR^1$, $OR^1$, $NR^1R^{12}$ or $OS(O)_rR^1$;

B is a 5-membered ring having one or two unsaturations containing 1, 2, 3 or 4 heteroatoms chosen from O, N and S provided that not more than one heteroatom is other than N, or a 6-membered aromatic ring containing 1 or 2 nitrogen atoms, either of which rings is optionally substituted by one or more substituents independently chosen from: $C_{1-6}$alkyl; $C_{1-6}$haloalkyl; $C_{1-6}$alkoxy; hydroxy; halogen; $S(O)_rR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano; and when the 5- or 6-membered ring contains an N atom, the N atom is optionally substituted by an O atom;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, aminocarbonyl, $C_{1-6}$alkylamino, di($C_{1-6}$alkyl)amino, $C_{1-6}$alkoxy, $C_{1-6}$alkylaminocarbonyl, di($C_{1-6}$alkyl)aminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom or by an oxo group on a carbon atom; aryl, aryl$C_{1-6}$alkyl, aryl$C_{2-6}$alkenyl or aryl$C_{2-6}$alkynyl optionally substituted on the aryl ring by $C_{1-6}$alkyl, halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$ cycloalkyl group;

$R^4$ is hydrogen, $C_{1-8}$alkyl, $C_{2-8}$alkenyl, $C_{2-8}$alkynyl, aryl or $CH_2(CO)_m NR^8 R^9$;

$R^5$ is $NR^6 R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{12}$ is hydrogen or $C_{1-6}$alkyl;

l is zero, 1 or 2;

m is zero or 1;

n is 0, 1 or 2;

p is zero, 1 or 2;

q is 0, 1 or 2; and r is 0, 1 or 2.

B is preferably a 5- or 6-membered optionally substituted heterocyclic aromatic ring.

Thus when B is an aromatic ring it may be a thiophene, thiazole, pyrimidine, oxazole, pyridine or pyrazine which is unsubstituted or substituted by $C_{1-6}$alkyl, hydroxy, $C_{1-6}$alkoxy or halogen, and, when present, a ring nitrogen of B is optionally substituted by an oxygen atom. When B is a 5- or 6-membered ring having one unsaturation it is preferably oxazolidinyl or imidazolinyl optionally substituted by halogen, hydroxy, $C_{1-6}$alkoxy or $C_{1-4}$alkyl. Favoured substituents of B are hydroxy and $C_{1-6}$alkoxy and particularly hydroxy and methoxy.

Particular embodiments of B are pyrid-2-yl, N-oxy-pyrid-2-yl, thiazol-2-yl, pyrazin-2-yl, oxazol-2-yl, pyrid-3-yl, pyrid-4-yl, pyrimidin-2-yl, and thiophen-2-yl.

$R^1$ may be hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^1$ is preferably $C_{1-6}$alkyl, $C_{2-6}$alkenyl or $C_{3-6}$cycloalkyl each of which is optionally substituted by amino, di($C_{1-6}$alkyl)amino, hydroxy, $C_{1-6}$alkoxy, $C_{1-6}$alkylaminocarbonyl or one, two or three halogen atoms; aryl or aryl$C_{1-6}$alkyl optionally substituted on the aryl ring by a halogen atom, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, either of which rings is optionally substituted by halogen, $C_{1-6}$alkoxy, $C_{1-6}$alkylthio, aryl or $C_{1-6}$alkyl.

More preferably $R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, isoxazole, tetrazole, thiophene, furan, thiazole, imidazole, triazole or thiadiazole, each of which is unsubstituted or substituted by $C_{1-4}$alkyl, phenyl, fluorine, chlorine or $C_{1-4}$alkylthio. More preferably $R^1$ is $C_{1-6}$alkyl optionally substituted by one, two or three fluorine atoms; phenyl optionally substituted by chlorine, thiazole, imidazole, triazole or thiadiazole each of which is unsubstituted or substituted by $C_{1-4}$alkyl or chlorine.

A may be $S(O)_p(CH_2)_n R^1$, $OS(O)_l R^1$, $OR^1$ or $C_{1-6}$alkyl.

A may be $S(O)_p R^1$ or $OR^1$, preferably $S(O)_p R^1$.

When A is not $S(O)_p R^1$, $OR^1$ or $NR^1 R^{14}$ it is preferably $C_{1-6}$alkyl, $C_{2-6}$alkenyl or $C_{3-6}$cycloalkyl.

When A is $OR^1$, $R^1$ is generally $C_{1-6}$alkyl optionally substituted by $C_{1-4}$alkoxy, $C_{3-6}$cycloalkyl or aryl.

Particular embodiments of A are ethylthio, benzylthio, (1-methyl-1,2,4-triazol-3-yl)methylthio and methylthio.

Further particular embodiments of A are thiophen-2-ylthio, (2-methylfuran-3-yl)thio, 1,2,4-triazol-4-ylmethylthio, imidazol-4-ylmethylthio, phenylthio, (5-methoxy-1,2,4-oxadiazol-3-yl)methylthio, trifluoromethylsulphonyloxy, (2-methylthiazol-4-yl)methylthio, (5-methylisoxazol-3-yl)methylthio, n-propylamino, 1,2,4-triazol-3-ylmethylthio, pyrid-2-ylmethylthio, thiazol-4-ylmethylthio, 2,2,2-trifluoroethylthio, 2-hydroxyethylthio, (5-chloro-1,2,3-thiadiazol-4-yl)methylthio, benzyloxy, thiophen-2-ylsulphonyloxy, (1-methylimidazol-2-yl)methylthio, isopropylamino, (1-methyltetrazol-5-yl)methylthio, (4-methylphenyl)sulphonyloxy, imidazol-2-ylmethylthio and ethyl.

Still further particular embodiments of A are (1,2,3-triazol-4-yl)methylthio, pyrid-4-ylmethylthio, imidazol-4-ylmethylthio, pyrid-3-ylmethylthio, 2-methoxyethylthio, 3-thiopropionamide, N,N-dimethyl-2-thioethylamine, N,N-dimethyl-3-thiopropylamine, 4-methylphenylsulfonyloxy, 3-thiopropylamine, 5-thiomethyloxazolidin-2-one and N,N-dimethyl-2-thioacetamide.

$R^2$ and $R^3$ are preferably independently chosen from hydrogen and methyl or are attached to the same carbon atom and together with that atom form a $C_{3-6}$cycloalkyl group. More preferably both are methyl or $R^2$ is hydrogen and $R^3$ is methyl. Most preferably $R^2$ is hydrogen and $R^3$ is methyl. Preferably $R^2$ and $R^3$ are geminal to each other, preferably at the 6-position, i.e. beta to the carbonyl group in formula I.

$R^4$ may by hydrogen, $C_{1-4}$alkyl, $C_{2-4}$alkenyl, $C_{2-4}$alkynyl, aryl or $CH_2(CO)_m NR^8 R^9$. $R^4$ is preferably hydrogen, $C_{1-4}$alkyl or $CH_2(CO)_m NR^8 R^9$, more preferably hydrogen, methyl or $CH_2 CONR^8 R^9$ and most preferably methyl or $CH_2 CONR^8 R^9$.

$R^5$ is preferably methyl, methoxy, ethoxy or $NR^6 R^7$ and most preferably methyl, ethoxy or $NR^6 R^7$.

$R^6$ may be hydrogen, $C_{1-4}$alkyl, $C_{2-4}$alkenyl, $C_{2-4}$alkynyl, aryl or $CH_2(CO)_m NR^8 R^9$. $R^6$ is preferably hydrogen or $C_{1-4}$alkyl and most preferably hydrogen.

$R^7$ is preferably phenyl unsubstituted or substituted by halogen, nitro or cyano, more preferably optionally substituted by halogen, such as chlorine.

$R^8$ is preferably hydrogen or $C_{1-6}$alkyl and most preferably hydrogen.

$R^9$ is preferably $C_{1-6}$alkyl or phenyl unsubstituted or substituted by one, two or three substituents independently chosen from halogen, nitro and cyano, more preferably $C_{1-6}$alkyl or phenyl optionally substituted by one or two substituents independently chosen from halogen and nitro and most preferably tert-butyl or phenyl optionally substituted with one or two substituents chosen from chlorine and nitro, such as 4-chlorophenyl.

$R^{12}$ is generally hydrogen or $C_{1-4}$alkyl and most preferably hydrogen.

l is preferably 2.

m is preferably 1.

n is preferably zero or 1. n may be zero. n may be 1.

p is preferably zero or two, most preferably zero.

q is preferably 1.

r is preferably 1.

A subclass of compounds according to the present invention comprises a compound of formula I, or a pharmaceutically acceptable salt thereof, wherein:

A is $S(O)_p(CH_2)_n R^1$, $OS(O)_r R^1$, $OR^1$, $NR^1 R^{12}$ or $C_{1-6}$alkyl;

B is a thiophene, thiazole, pyrimidine, oxazole, pyridine or pyrazine which is unsubstituted or substituted by $C_{1-6}$alkyl, $C_{1-6}$alkoxy, hydroxy or halogen and, when present, a ring nitrogen of B is optionally substituted by an oxygen atom;

$R^1$ is $C_{1-6}$alkyl optionally substituted by one, two or three fluorine atoms; phenyl optionally substituted by chlorine, fluorine or methoxy; or pyridine, isoxazole, tetrazole, thiophene, furan, thiazole, imidazole, triazole or thiadiazole each of which is unsubstituted or substituted by $C_{1-4}$alkyl or chlorine;

$R^2$ and $R^3$ are independently hydrogen or methyl;

$R^{12}$ is hydrogen or $C_{1-16}$alkyl;

l is 2, n is zero or 1, p is zero or 2 q is 1; and r is 1.

The above preferred definitions of the substituent apply *mutatis mutandis* to this subclass also.

Specific compounds of the present invention are:

8-ethylthio-3-methyl-5-(pyrid-2-yl)-1,2,3,4-tetrahydronaphthalen-1-one;

8-ethylthio-3-methyl-5-(oxazol-2-yl)-1,2,3,4-tetrahydronaphthalen-1-one;

8-ethylthio-3-methyl-5-(pyrimidin-5-yl)-1,2,3,4-tetrahydronaphthalen-1-one;

8-ethylthio-3-methyl-5-(pyrid-4-yl)-1,2,3,4-tetrahydronaphthalen-1-one;

8-ethylthio-3-methyl-5-(pyrid-3-yl)-1,2,3,4-tetrahydronaphthalen-1-one;

8-ethylthio-3-methyl-5-(pyrazin-2-yl)-1,2,3,4-tetrahydronaphthalen-1-one;

8-ethylthio-3-methyl-5-(thiazol-2-yl)-1,2,3,4-tetrahydronaphthalen-1-one;

8-benzylthio-3-methyl-5-(pyrid-2-yl)-1,2,3,4-tetrahydronaphthalen-1-one;

3-methyl-8-(1-methyl-1,2,4-triazol-3-yl)methylthio-5-(thiazol-2-yl)-1,2,3,4-tetrahydronaphthalen-1-one;

3,3-dimethyl-8-methylthio-5-(pyrid-2-yl)-1,2,3,4-tetrahydronaphthalen-1-one;

and the pharmaceutically acceptable salts thereof.

Preferably the compositions according to the present invention are in unit dosage forms such as tablets, pills, capsules, powders, granules, solutions or suspensions, or suppositories, for oral, parenteral or rectal administration, by inhalation or insufflation or administration by transdermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the $\alpha 5$ subunit. In particular, they are desirably inverse agonists of the $\alpha 5$ subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal, delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium, delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $\alpha 2$ or $\alpha 3$ subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder, bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha 5$ subunit, in particular for conditions requiring cognition enhancement such as Alzheimer's disease.

There is also disclosed a method of treatment or prevention of a condition associated with $GABA_A$ receptors containing the $\alpha 5$ subunit which comprises administering to a subject suffering from or prone to such a condition a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{2-6}$alkenyl", "$C_{2-6}$alkynyl", "$C_{1-4}$alkyl", "$C_{2-4}$alkenyl", "$C_{2-4}$alkynyl" and "$C_{1-6}$alkoxy" are to be construed in an analogous manner.

The expression "$C_{3-6}$cycloalkyl" includes cyclopropyl, cyclobutyl, cyclopentyl and cyclohexyl groups. "$C_{5-6}$cycloalkenyl", "$C_{3-8}$cycloalkyl" and "$C_{5-7}$cycloalkyl" are to be construed analogously.

Suitable 5- and 6-membered heteroaromatic rings include thiophene, pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine, especially fluorine, chlorine and bromine.

The expression "aryl$C_{1-6}$alkyl" as used herein includes benzyl, phenylethyl, phenylpropyl and naphthylmethyl. "Aryl$C_{2-6}$alkenyl" and "aryl$C_{2-6}$alkynyl" should be construed in an analogous fashion.

Typical aryl groups include phenyl and naphthyl. Preferably the aryl is phenyl.

For use in medicine, the salts of the compounds of formula (I) will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a novel compound of formula (I) or a pharmaceutically acceptable salt thereof as defined above. The skilled person will appreciate that the alternative and preferred embodiments of these compounds in the pharmaceutical compositions described above are also alternative and preferred embodiments of the novel compounds of formula (I) provided by the present invention.

Aptly novel compounds of this invention include those wherein p is 1 or 2.

Aptly novel compounds of this invention include those wherein $R^1$ is not methyl.

Aptly novel compounds of this invention include those wherein $R^4$ is not hydrogen, methyl or $CH_2(CO)_m NR^8 R^9$.

The present invention also provides a process for producing a compound of formula I, or a pharmaceutically acceptable salt thereof, which comprises:

(i) where A is $C_{1-6}$alkyl, $C_{2-6}$alkenyl, $C_{2-6}$alkynyl, $C_{3-6}$cycloalkyl, aryl$C_{1-6}$alkyl or aryl, converting the bromine atom in a compound of formula II:

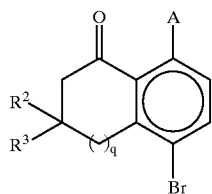

(II)

wherein A is $C_{1-6}$alkyl, $C_{2-6}$alkenyl, $C_{2-6}$alkynyl, $C_{3-6}$cycloalkyl, aryl$C_{1-6}$alkyl or aryl and $R^2$, $R^3$ and q are as defined above, into a group B as defined above by standard techniques; or (ii) where A is $OS(O)_t R^1$, reacting a compound of formula II in which A is OH with a compound of formula III:

$R^1 S(O)_p (CH_2)_n Cl$ (III)

wherein $R^1$, n and p are as defined above, generally in the presence of a base such as $Et_3N$ and a solvent such as DCM and converting the bromine atom of the compound of formula II into a group B as defined above by standard techniques; or (iii) where A is $OR^1$, converting the bromine in a compound of formula II, in which A is OH, into a group B as defined above by standard techniques and reacting with a compound of formula IV:

$R^1-Br$ (IV)

wherein $R^1$ is as defined above, generally in a base such as NaH and a solvent such as DMF; or (iv) where A is $NR^1 R^{12}$, reacting a compound of formula I in which A is $OS(O)_2 R^1$ with a compound of formula V:

$HNR^1 R^{12}$ (V)

wherein $R^1$ and $R^{12}$ are as defined above, generally in a sealed tube at a temperature of about 100° C.; or (v) where A is $SR^1$, reacting a compound of formula II in which A is OH with $Me_2NCSCl$ in the presence of a base such as DABCO and in a solvent such as DMF to produce a compound of formula VI:

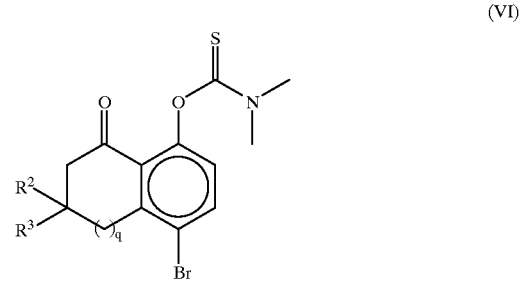

(VI)

wherein $R^2$, $R^3$ and q are as defined above, then heating in the presence of a basic solvent such as $PhNMe_2$ generally at reflux to produce a compound of formula VII:

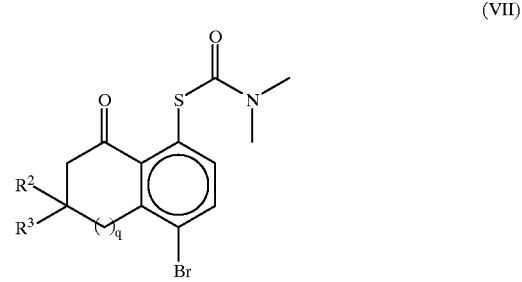

(VII)

wherein $R^2$, $R^3$ and q are as defined above, then heating generally to reflux in the presence of a base such as KOH in MeOH followed by the addition of a compound of formula IX:

Hal–$R^1$ (IX)

wherein $R^1$ is as defined above and Hal is a halogen atom such as bromine, chlorine or iodine to give a compound of formula X:

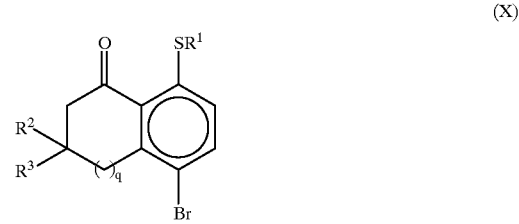

(X)

wherein $R^1$, $R^2$, $R^3$ and q are as defined above, followed by converting the bromine in the compound of formula X into a group B as defined above by standard techniques; and (vi) optionally converting the thus obtained compound of formula I into another compound of formula I by standard techniques; and (vii) optionally converting the thus obtained compound of formula I into a pharmaceutically acceptable salt thereof if in free base form, or into the free base or another pharmaceutically acceptable salt thereof if in salt form.

The compound of formula II in which A is OH can be made by reacting a compound of formula II in which A is OMe with BBr$_3$ in a solvent such as DCM generally at 0° C. Compounds of formula II in which A is C$_{1-6}$alkyl, C$_{2-6}$alkenyl, C$_{2-6}$alkynyl, C$_{3-6}$cycloalkyl, arylC$_{1-6}$alkyl or aryl can be made by adapting the methods disclosed herein for making other compounds of formula II or by standard interconversions from other compounds of formula II.

The compound of formula II in which A is OMe can be made by reacting a compound of the formula XI:

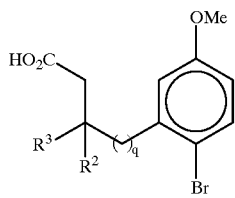

(XI)

wherein R$^2$, R$^3$ and q are as defined above, with a compound such as polyphosphoric acid generally at 100° C.

The compound of formula XI in which R$^2$ is hydrogen can be made by reacting a compound of formula XII:

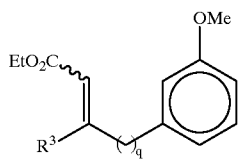

(XII)

wherein R$^3$ and q are as defined above successively with a hydrogenating reagent such as palladium on carbon in the presence of hydrogen gas at about 50 psi, a base such as KOH in a solvent such as ethanol/water generally at reflux, and a brominating agent such as Br$_2$ in a solvent such as DCM.

The compound of formula XII can be made by reacting a compound of formula XIII:

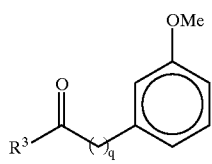

(XIII)

wherein R$^3$ and q are as defined above with a reagent such as (carbethoxymethylene)triphenylphosphorane generally at 140° C.

The compound of formula XI in which R$^2$ is C$_{1-6}$alkyl can be made by reacting a compound of formula XIV:

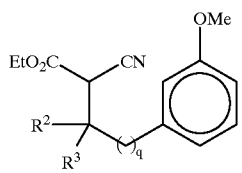

(XIV)

in which R$^2$ is C$_{1-6}$alkyl and R$^3$ and q are as defined above, successively with a base such as KOH in a solvent such as ethylene glycol, and a brominating agent such as Br$_2$ in a solvent such as DCM.

The compound of formula XIV can be made by reacting a compound of formula XV:

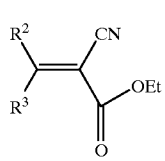

(XV)

wherein R$^2$ is C$_{1-6}$alkyl and R$^3$ are as defined above with a compound of formula XVI:

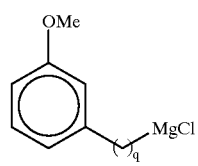

(XVI)

wherein q is as defined above, generally in the presence of a solvent such as THF for about 2 h.

Compounds of formula XIII, XIV and XV are available commercially or can be made from commercially available compounds by standard techniques.

Further details of the above reactions can be found, for example, in Comprehensive Organic Syntheses, ed. B. M. Trost, Pergamon Press, Oxford.

Compounds of formula I in which A is SR$^1$ can also be obtained by reacting a compound of formula I in which A is S(O)$_p$R$^1$ where p is one or two and R$^1$ is as defined above with a thiol in the presence of a base. In a particular embodiment of this method a compound of formula I in which B is pyridyl, for example pyrid-2-yl, and A is, for example, methylthio, is oxidised using m-CPBA generally in three equivalents, usually in the presence of a base, such as DCM, and a solvent, such as dioxan, to yield the sulphonyl/pyridinone derivative. This compound is then reacted with the appropriate thiol, generally in the form of the sodium salt and in the presence of a solvent such as THF to yield a compound of formula I wherein A is of the desired formula SR$^1$ and B is a pyridinone group. The pyridinone is then reduced by reacting with PPh$_3$ at elevated temperature, i.e. at about 200°, to yield a compound of formula I wherein SR$^1$ is as desired and B is pyridyl.

Compounds of formula I in which A is C$_{1-6}$alkyl, C$_{2-6}$alkenyl, C$_{2-6}$alkynyl or C$_{3-6}$cycloalkyl can also be obtained by reacting a compound of formula I in which A is S(O)$_p$R where p is zero or two with an appropriate Grignard reagent.

Compounds of formula I in which A is OR$^1$ can also be obtained by reacting a compound of formula I in which A is $S(O)_pR^1$ and p is one or two with an alcohol in the presence of a strong base.

Compounds of formula I in which A is $NR^1R^{14}$ can also be obtained by reacting a compound of formula I in which A is $S(O)_pR^1$ and p is one or two with an amine.

It will be understood that the above transformations of $S(O)_pR^1$ are illustrative and other standard techniques known to the skilled person may alternatively be used. The above reactions are illustrated in the Examples.

Compounds of formulae III, IV, V and IX are known in the art or can be made by known methods from known starting materials.

The following Examples illustrate pharmaceutical compositions according to the invention.

COMPOSITION EXAMPLE 1A

Tablets Containing 1–25 mg of Compound

|  | Amount mg | | |
|---|---|---|---|
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

COMPOSITION EXAMPLE 1B

Tablets Containing 26–100 mg of Compound

|  | Amount mg | | |
|---|---|---|---|
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

COMPOSITION EXAMPLE 2

Parenteral Injection

| Active Ingredient(s) | Amount<br>1 to 100 mg |
|---|---|
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

COMPOSITION EXAMPLE 3

Topical Formulation

| Active Ingredient(s) | Amount<br>1–10 g |
|---|---|
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human $GABA_A$ receptors containing the cc5 subunit stably expressed in Ltk cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells; 10 nM for α5β3γ2 cells) in assay buffer.

Flunitrazepam 100 µM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 µl of assay buffer.

50 µl of [$^3$H]-flumazenil (final concentration for α1β3γ2: 1.8 nM; for α2β3γ2: 1.8 nM; for α3β3γ2: 1.0 nM; for α5β3γ2: 1.0 nM).

50 µl of buffer or solvent carrier (e.g. 10% DMSO) if compounds are dissolved in 10% DMSO (total); test compound or flunitrazepam (to determine non-specific binding), 10 µM final concentration.

100 µl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]Ro 15-1788 from the α5 subunit of the human GABA$_A$ receptor of 300 nM or less, preferably of 100 nM or less, and more particularly of 50 nM or less.

The following Examples illustrate the present invention:

INTERMEDIATE 1

Dimethyl thiocarbamic acid S-(4-bromo-6-methyl-8-oxo-5,6,7,8-tetrahydronaphthalen-1-yl)ester Step 1: 5-Bromo-8-hydroxy-3-methyl-1,2,3,4-tetrahydronaphthalen-1-one To a solution of 5-bromo-8-methoxy-3-methyl-1,2,3,4-tetrahydronaphthalen-1-one (32.2 g 0.12 mol) in DCM (400 mL) at 0° C. was added boron tribromide (119 mL of a 1.0 M solution in DCM, 0.12 mol) dropwise. The mixture was stirred at 5° C. for 1 h then water (50 mL) was added cautiously. The mixture was washed with water (3×200 mL) then the organic layer was separated, dried (Na$_2$SO$_4$) and evaporated. The residue was chromatographed on silica gel, eluting with hexane: DCM (100:0-1:1), to afford the phenol (23.5 g, 77%). $^1$H NMR (250 MHz, CDCl$_3$) δ 1.18 (3H, d, J=6.1 Hz), 2.22–2.55 (3H, m), 2.69–2.77 (1H, m), 3.14–3.23 (1H, m), 6.74 (1H, d, J=8.9 Hz), 7.59 (1H, d, J=8.9 Hz), 12.54 (1H, s)

Step 2: Dimethyl thiocarbamic acid O-(4-bromo-6-methyl-8-oxo-5,6,7,8-tetrahydronaphthalen-1-yl)ester To a solution of the phenol (23.5 g, 0.09 mol) in DMF (200 mL) was added dimethylthiocarbamoyl chloride (34.2 g, 0.28 mol) and 1,4-diazabicyclo[2.2.2]octane (31 g, 0.28 mol). The solution was stirred for 4 h then poured into ice/water (500 mL) and extracted with DCM (4×200 mL). The combined organic layers were dried (Na$_2$SO$_4$) and evaporated and the residue chromatographed on silica gel, eluting with hexane: DCM (100:0-9:1). The O-arylthiocarbamate (21.4 g, 68%) was isolated as a yellow oil. $^1$H NMR (360 MHz, CDCl$_3$) δ 1.16 (3H, d, J=6.1 Hz), 2.27–2.36 (2H, m), 2.53–2.67 (2H, m), 3.18–3.21 (1H,m), 3.41 (3H, s), 3.46 (3H, s), 6.86 (1H, d, J=8.6 Hz), 7.74 (1H, d, J=8.6 Hz). MS (ES$^+$) 342/344 (M+1).

Step 3: Dimethyl thiocarbamic acid S-(4-bromo-6-methyl-8-oxo-5,6,7,8-tetrahydronaphthalen-1-yl) ester A solution of the O-arylthiocarbamate (21.4 g, 0.063 mol) in N,N-dimethylaniline (150 mL) was heated at reflux for 8 h. The mixture was cooled to room temperature and chromatographed directly on silica gel, eluting with hexane:DCM (100:0-1:1) followed by DCM-MeOH (95:5). The S-arylthiocarbamate (12.5 g, 58%) was isolated as a beige solid. $^1$H NMR (360 MHz, CDCl$_3$) δ 1.17 (3H, d, J=6.2 Hz), 2.32–2.44 (2H, m), 2.50–2.58 (1H, m), 2.69–2.74 (1H, m), 2.98–3.20 (6H, m), 3.21–3.30 (1H, m), 7.40 (1H, d, J=8.4 Hz), 7.65 (1H, d, J=8.4 Hz). MS (ES+) 342/344 (M+1).

INTERMEDIATE 2

5-Bromo-8-ethylthio-3-methyl-1,2,3,4-tetrahydronaphthalen-1-one

A solution of Intermediate 1 (3.0 g, 8.8 mmol) in MeOH (125 mL) was degassed with nitrogen for 30 min, then KOH (3.7 g, 66 mmol) was added and the solution heated at reflux for 10 min. The mixture was removed from the oil bath and after 5 min iodoethane (0.9 mL, 11 mmol) was added and the mixture stirred at room temperature for 3 h. The solvent was evaporated, water (50 mL) added and the mixture acidified with 1N HCl. The mixture was extracted with DCM (4×50 ml) and the combined organics dried (Na$_2$SO$_4$) and evaporated. The thioether (2.5 g, 95%) was isolated as a pink solid. $^1$H NMR (360 MHz, CDCl$_3$) δ 1.16 (3H, d, J=6.2 Hz), 1.39 (3H, t, J=7.4 Hz), 2.20–2.38 (2H,m), 2.50–2.58 (1H, m), 2.72–2.77 (1H, m), 2.89 (1H, q, J=7.4 Hz), 3.19–3.26 (1H, m), 7.06 (1H, d, J=8.7 Hz), 7.59 (1H, d, J=8.7 Hz). MS (ES+) 299/301 (M+1).

INTERMEDIATE 3

Dimethyl thiocarbamic acid S-(4-(thiazol-2-yl)-6-methyl-8-oxo-5,6,7,8-tetrahydronaphthalen-1-yl) ester Step 1: 8-Hydroxy-3-methyl-5-(thiazol-2-yl)-1,2,3,4-tetrahydronaphthalen-1-one A solution of 5-bromo-8-hydroxy-3-methyl-1,2,3,4-tetrahydronaphthalen-1-one (3.0 g, 0.012 mol) and 2-(tri-n-butylstannyl)thiazole (6.4 g, 0.17 mol) in dioxan (100 mL) was degassed with nitrogen for 30 min. Tetrakis (triphenylphosphine)palladium(0) (1 g) was added and the mixture heated at reflux for 48 h. The solvent was evaporated and the residue chromatographed on silica gel, eluting with EtOAc:hexane (1:4). The title compound (1.9 g, 62%) was isolated as a yellow oil. $^1$H NMR (360 MHz, CDCl$_3$) δ 1.13 (3H, d, J=6.5 Hz), 2.20–2.34 (1H, m), 2.39–2.47 (1H, m), 2.73–2.83 (2H, m), 3.34–3.49 (1H, m), 6.90 (1H, d, J=8.8 Hz), 7.40 (1H, d, J=3.3 Hz), 7.73 (1H, d, J=8.8 Hz), 7.89 (1H, d, J=3.3 Hz), 12.93 (1H, s). MS (ES$^+$) 260 (M+1).

Step 2: Dimethyl thiocarbamic acid O-(6-methyl-8-oxo-4-(thiazol-2-yl)-5,6,7,8-tetrahydronaphthalen-1-yl)ester In the same way as described in Intermediate 1, Step 2, using 8-hydroxy-3-methyl-5-(thiazol-2-yl)-1,2,3,4-tetrahydronaphthalen-1-one, the title compound (4.6 g, 78%) was isolated as a colourless solid. $^1$H NMR (360 MHz, CDCl$_3$) δ 1.10 (3H, d, J=6.3 Hz), 2.20–2.39 (2H, m), 2.64–2.69 (1H, m), 2.79–2.87 (1H, m), 3.29–3.35 (1H, m), 3.45 (3H, s), 3.48 (3H, s), 7.05 (1H, d, J=8.4 Hz), 7.45 (1H, d, J=3.4 Hz), 7.80 (1H, d, J=8.4 Hz), 7.95 (1H, d, J=3.4 Hz). MS (ES$^+$) 347 (M+1).

Step 3: Dimethyl thiocarbamic acid S-(4-(thiazol-2-yl)-6-methyl-8-oxo-5,6,7,8-tetrahydronaphthalen-1-yl)ester In the same way as described in Intermediate 1, Step 3, using dimethyl thiocarbamic acid O-(6-methyl-8-oxo-4-(thiazol-2-yl)-5,6,7,8-tetrahydronaphthalen-1-yl)ester, the title compound (3.3 g, 72%) was isolated as a yellow solid. $^1$H NMR (360 MHz, CDCl$_3$) δ 1.11 (3H, d, J=6.5 Hz), 2.20–2.34 (1H, m), 2.36–2.44 (1H, m), 2.74–2.81 (2H, m), 3.00–3.30 (6H, m), 3.32–3.38 (1H, m), 7.46 (1H, d, J=3.3 Hz), 7.64 (1H, d, J=8.2 Hz), 7.68 (1H, d, J=8.2 Hz), 7.95 (1H, d, J=3.3 Hz). MS (ES$^+$) 347 (M+1).

INTERMEDIATE 4

Dimethyl thiocarbamic acid S-(4-bromo-6,6-dimethyl-8-oxo-5,6,7,8-tetrahydronaphthalen-1-yl)ester Step 1: Ethyl 2-cyano-3,3-dimethyl-4-(3-methoxyphenyl) butanoate A solution of ethyl 2-cyano-3-methylcrotonate (10.8 g, 0.07 mol) in THF (100 mL) was added dropwise to a stirred ethereal solution of 3-methoxybenzylmagnesium chloride (prepared by adding a solution of 3-methoxybenzyl chloride (9.3 mL, 0.064 mol) in ether (48 mL) to a slurry of Mg (1.7 g, 0.07 mol) in ether (20 mL)). After addition the mixture was stirred at room temperature for a further 2 h then NH$_4$Cl (sat., 50 mL) was added. The solution was partitioned between EtOAc (200 mL) and water (200 mL) and the organic layer separated and dried (MgSO$_4$). The solvent was evaporated and the residue chromatographed on silica gel, eluting with petrol:EtOAc (5:1). The title compound (9.0 g, 51%) was isolated as a colourless oil. $^1$H NMR (360 MHz, CDCl$_3$) δ 1.10 (3H, s), 1.20 (3H, s), 1.33 (3H, t, J=7.1 Hz), 2.74 (1H, d, J=13.5 Hz), 2.78 (1H, d, J=13.5 Hz), 3.33 (1H, s), 3.81 (3H, s), 4.26 (2H, q, J=7.1 Hz), 6.72–6.82 (3H, m), 7.22 (1H, t, J=7.8 Hz). MS (ES$^+$) 276 (M+1).

Step 2: 3,3-Dimethyl-4-(3-methoxyphenyl)butanoic acid

A solution of ethyl 2-cyano-3,3-dimethyl-4-(3-methoxyphenyl)butanoate (9.0 g, 0.033 mol) and KOH (9.2 g, 0.163 mol) in ethylene gylcol (100 mL) was heated at 180° C. for 2 days. The solution was cooled to room temperature, poured into water (200 mL) and extracted with ether (100 mL). The organic layer was separated, dried (MgSO$_4$) and evaporated to afford the acid (6.7 g, 0.03 mol)as brown oil, which was used without further purification. $^1$H NMR (360 MHz, CDCl$_3$) δ 1.06 (6H, s), 2.24 (2H, s), 2.66 (2H, s), 3.81 (3H, s), 6.74–6.79 (3H, m), 7.19 (1H, t, J=8.1 Hz). MS (ES$^+$) 223 (M+1).

Step 3: 4-(2-Bromo-5-methoxyphenyl)-3,3-dimethylbutanoic acid

To a solution of 3,3-dimethyl-4-(3-methoxyphenyl) butanoic acid (6.7 g, 0.03 mol) in DCM (100 mL) at 0° C. was added a solution of bromine (1.55 mL, 0.03 mol) in DCM (13 mL) dropwise. After addition the solution was stirred at 0° C. for 1 h then the solution was washed with water (3×100 mL), dried (Na$_2$SO$_4$) and evaporated. The product (8.45 g, 94%) was isolated as a brown oil and used without further purification. $^1$H NMR (360 MHz, CDCl$_3$) δ 1.12 (6H, s), 2.36 (2H, s), 2.98 (2H, s), 3.80 (3H, s), 6.65 (1H, dd, J=8.7 and 3.1 Hz), 6.85 (1H, d, J=3.1 Hz), 7.43 (1H, d, J=8.7 Hz).

Step 4: 5-Bromo-3,3-dimethyl-8-methoxy-1,2,3,4-tetrahydronaphthalen-1-one

The acid (8.45 g, 0.028 mol) and polyphosphoric acid (86 g) were stirred and heated at 100° C. for 30 min. After this time the mixture was poured into water (150 mL) and extracted with DCM (4×100 mL). The combined organic layers were washed with NaHCO$_3$ (sat., 2×100 mL) and brine (2×100 mL). The organic layer was separated, dried (MgSO$_4$) and evaporated. The residue was chromatographed on silica gel, eluting with hexane:EtOAc (1:1) to give the tetralone (3.0 g, 38%) as a beige solid. $^1$H NMR (250 MHz, CDCl$_3$) δ 1.09 (6H, s), 2.48 (2H, s), 2.86 (2H, s), 4.18 (3H, s), 6.86 (1H, d, J=9.0 Hz), 7.65 (1H, d, J=9.0 Hz). MS (ES$^+$) 283/285 (M+1).

Step 5: 5-Bromo-3,3-dimethyl-8-hydroxy-1,2,3,4-tetrahydronaphthalen-1-one

In the same way as described in Intermediate 1, Step 1, using 5-bromo-3,3-dimethyl-8-methoxy-1,2,3,4-tetrahydronaphthalen-1-one, the phenol (2.06 g, 72%) was isolated as a yellow solid. mp 65–67° C. $^1$H NMR (360 MHz, CDCl$_3$) δ 1.11 (6H, s), 2.54 (2H, s), 2.84 (2H, s), 6.75 (1H, d, J=8.9 Hz), 7.60 (1H, d, J=8.9 Hz), 12.48 (1H, s).

Step 6: Dimethyl thiocarbamic acid O-(4-bromo-6,6-dimethyl-8-oxo-5,6,7,8-tetrahydronaphthalen-1-yl)ester In the same way as described in Intermediate 1, Step 2, using 5-bromo-3,3-dimethyl-8-hydroxy-1,2,3,4-tetrahydronaphthalen-1-one, the carbamate (2.39 g, 88%) was isolated as a pale yellow solid. mp 114–116° C. $^1$H NMR (360 MHz, CDCl$_3$) δ 1.10 (6H, s), 2.44 (2H, s), 2.90 (2H, s), 3.42 (3H, s), 3.46 (3H, s), 6.87 (1H, d, J=8.6 Hz), 7.75 (1H, d, J=8.6 Hz). MS (ES$^+$) 356/358 (M+1).

Step 7: Dimethyl thiocarbamic acid S-(4-bromo-6,6-dimethyl-8-oxo-5,6,7,8-tetrahydronaphthalen-1-yl)ester In the same way as described in Intermediate 1, Step 3, using dimethyl thiocarbamic acid O-(4-bromo-6,6-dimethyl-8-oxo-5,6,7,8-tetrahydronaphthalen-1-yl)ester, the carbamate (1.94 g, 81%) was isolated as a pink solid. mp 143–145° C. $^1$H NMR (360 MHz, CDCl$_3$) δ 1.11 (6H, s), 2.55 (2H,s), 2.91 (2H, s), 2.97–3.21 (6H, m), 7.41 (1H, d, J=8.4 Hz), 7.66 (1H, d, J=8.4 Hz). MS (ES$^+$) 356/358 (M+1).

EXAMPLE 1

8-Ethylthio-3-methyl-5-(pyridin-2-yl)-1,2,3,4-tetrahydronaphthalen-1-one

To a solution of Intermediate 2 (200 mg, 0.67 mol) in dioxan (20 mL) was added 2-(tributylstannyl)pyridine (369 mg, 1.0 mmol) and the mixture degassed with nitrogen for 30 min. Tetrakis(triphenylphosphine)palladium(0) (150 mg) was added and the mixture heated at reflux for 20 h. The solvent was evaporated, EtOAc:hexane (1:1) added, and the mixture filtered. The filtrate was evaporated and the residue chromatographed on silica gel, eluting with hexane:EtOAc (95:5–85:15), to give the title compound (55 mg, 28%) as a cream solid. mp 120–122° C. C$_{18}$H$_{19}$NOS requires: C, 72.69; H, 6.44; N, 4.71%. Found: C, 72,76; H, 6.36; N, 4.65%. $^1$H NMR (360 MHz, CDCl$_3$) δ 1.04 (3H, d, J=6.5 Hz), 1.42 (3H, t, J=7.4 Hz), 2.10–2.25 (1H, m), 2.32–2.40 (1H, m), 2.64–2.81 (2H, m), 2.92–2.98 (3H, m), 7.26–7.31 (2H, m), 7.38 (1H, d, J=7.9 Hz), 7.48 (1H, d, J=8.4 Hz), 7.77 (1H, d of t, J=7.8 and 1.8 Hz), 8.70–8.74 (1H, m). MS (ES$^+$) 298 (M+1).

EXAMPLE 2

8-Ethylthio-3-methyl-5-(oxazol-2-yl)-1,2,3,4-tetrahydronaphthalen-1-one

In the same way as described in Example 1, using 2-(tributylstannyl)oxazole, the title compound (50 mg, 31%) was isolated as a yellow solid. mp 111–113° C. C$_{16}$H$_{17}$NO$_2$S requires: C, 66.87; H, 5.96; N, 4.87%. Found: C, 66.82; H, 5.95; N, 4.47%. $^1$H NMR (360 MHz, CDCl$_3$) δ 1.16 (3H, d, J=6.5 Hz). 1.42 (3H, t, J=7.3 Hz), 2.18–2.32 (1H, m), 2.36–2.44 (1H, m), 2.76–2.99 (4H, m), 3.65–3.72 (1H, m), 7.29 (1H, s), 7.31 (1H, d, J=8.7 Hz), 7.76 (1H, s), 7.98 (1H, d, J=8.7 Hz). MS (ES$^+$) 288 (M+1).

EXAMPLE 3

8-Ethylthio-3-methyl-5-(pyrimidin-5-yl)-1,2,3,4-tetrahydronaphthalen-1-one

A solution of Intermediate 2 (250 mg, 0.84 mmol), 5-pyrimidine boronic acid (416 mg, 3.4 mmol) and Na$_2$CO$_3$ (534 mg, 5.0 mmol) in ethylene gylcol dimethyl ether (25 mL) and water (10 mL) was degassed with nitrogen for 1 h. Tetrakis(triphenylphosphine)palladium(0) (250 mg) was added and the mixture heated at reflux for 6 h. K$_2$CO$_3$ (10%, 25 mL) was added and the mixture filtered. The filtrate was extracted with EtOAc (2×20 mL) and the combined organic layers dried (Na$_2$SO$_4$) and evaporated. The residue was chromatographed on silica gel, eluting with hexane:EtOAc (3:1–3:2), to give the title compound (140 mg, 56%) as a yellow solid. mp 168–171° C. C$_{17}$H$_{18}$N$_2$OS 0.25 (H$_2$O) requires: C, 67.41; H, 6.16; N, 9.25%. Found: C, 67.72; H, 5.95; N, 9.03%. $^1$H NMR (360 MHz, CDCl$_3$) δ 1.06 (3H, d, J=6.5 Hz), 1.43 (3H, t, J=7.4 Hz), 2.14–2.26 (1H, m), 2.36–2.42 (1H, m), 2.53–2.61 (1H, m), 2.76–2.79 (1H, m), 2.81–2.84 (1H, m), 2.95 (2H, q, J=7.4 Hz), 7.29 (1H, d, J=8.4 Hz), 7.34 (1H, d, J=8.4 Hz), 8.74 (2H, s), 9.25 (1H, s). MS (ES$^+$) 299 (M+1).

EXAMPLE 4

8-Ethylthio-3-methyl-5-(pyridin-4-yl)-1,2,3,4-tetrahydronaphthalen-1-one

In the same way as described in Example 3, using 4-pyridylboronic acid, the title compound (80 mg, 32%) was isolated as a pale yellow solid. mp 145–147° C. C$_{18}$H$_{19}$NOS requires: C, 72.69; H, 6.44; N, 4.71%. Found: C, 72.43; H, 6.30; N, 4.61%. $^1$H NMR (360 MHz, CDCl$_3$) δ 1.04 (3H, d, J=6.5 Hz), 1.43 (3H, t, J=7.4 Hz), 2.10–2.24 (1H, m), 2.32–2.40 (1H, m), 2.51–2.58 (1H, m), 2.76–2.85 (2H, m), 2.96 (2H, q, J=7.4 Hz), 7.23–7.25 (2H, m), 7.28–7.29 (2H, m), 8.66–8.68 (2H, m). MS (ES$^+$) 298 (M+1).

EXAMPLE 5
8-Ethylthio-3-methyl-5-(pyridin-3-yl)-1,2,3,4-tetrahydronaphthalen-1-one In the same way as described in Example 1, using 3-(tributylstannyl)pyridine, the title compound (65 mg, 26%) was isolated as a colourless solid. mp 140–142° C. $C_{18}H_{19}NOS$. 0.1 ($H_2O$) requires; C, 72.25; H, 6.47; N, 4.68%. Found; C, 72.20; H, 6.47; N, 4.47%. $^1$H NMR (360 MHz, CDCl$_3$) δ 1.03 (3H, d, J=6.4 Hz), 1.43 (3H, t, J=7.3 Hz), 2.11–2.24 (1H, m), 2.31–2.40 (1H, m), 2.50–2.57 (1H, m), 2.76–2.83 (2H, m), 2.95(2H, q, J=7.3 Hz), 7.29–7.31 (2H, m), 7.38 (1H, dd, J=7.4 and 4.8 Hz), 7.62 (1H, d of t, J=7.9 and 2.0 Hz), 8.59 (1H, d, J=2.0 Hz), 8.63 (1H, dd, J=7.9 and 2.0 Hz). MS (ES$^+$) 298 (M+1).

EXAMPLE 6
8-Ethylthio-3-methyl-5-(pyrazin-2-yl)-1,2,3,4-tetrahydronaphthalen-1-one In the same way as described in Example 1, using 2-(tributylstannyl)pyrazine, the title compound was isolated (85 mg, 34%) as a pale yellow solid. mp 152–154° C. $C_{17}H_{18}N_2OS.0.25(H_2O)$ requires: C, 67.41; H, 6.16, N, 9.25%. Found: C, 67.46; H, 6.10; N, 8.88%. $^1$H NMR (360 MHz, CDCl$_3$), δ 1.06 (3H, d, J=6.5 Hz), 1.42 (3H, t, J=7.4 Hz), 2.13–2.25 (1H, m), 2.34–2.43 (1H, m), 2.70–2.82 (2H, m), 2.93–2.99 (3H, m), 7.34 (1H, d, J=8.4 Hz), 7.50 (1H, d, J=8.4 Hz), 8.59 (1H, d, J=1.8 Hz), 8.69–8.76 (2H, m). MS (ES$^+$) 299 (M+1).

EXAMPLE 7
8-Ethylthio-3-methyl-5-(thiazol-2-yl)-1,2,3,4-tetrahydronaphthalen-1-one In the same way as described in Example 1, using 2-(tributylstannyl)thiazole, the title compound (75 mg, 38%) was isolated as a yellow solid. mp 117–118° C. $C_{16}H_{17}NOS_2.0.1$ ($H_2O$) requires: C, 62.96; H, 5.68; N, 4.59%. Found: C, 62.91; H, 5.62; N, 4.25%. $^1$H NMR (360 MHz, CDCl$_3$), δ 1.11 (3H, d, J=6.4 Hz), 1.42 (3H, t, J=7.3 Hz), 2.16–2.26 (1H, m), 2.34–2.43 (1H, m), 2.75–2.85 (2H, m), 2.94 (2H, q, J=7.3 Hz), 3.34–3.40 (1H, m), 7.29 (1H, d, J=8.5 Hz), 7.43 (1H, d, J=3.3 Hz), 7.67 (1H, d, J=8.5 Hz), 7.94 (1H, d, J=3.3 Hz). MS (ES$^+$) 304 (M+1).

EXAMPLE 8
8-Benzylthio-3-methyl-5-(pyridin-2-yl)-1,2,3,4-tetrahydronaphthalen-1-one
Step 1: 8-Benzylthio-5-bromo-3-methyl-1,2,3.4-tetrahydronaphthalen-1-one In the same way as described for Intermediate 2, using benzyl bromide, the title compound (200 mg, 63%) was isolated. $^1$H NMR (250 MHz, CDCl$_3$) δ 1.16 (3H, d, J=6.2 Hz), 2.18–2.40 (2H, m), 2.48–2.59 (1H, m), 2.72–2.78 (1H, m), 3.19–3.27 (1H, m), 4.11 (2H, s), 7.12 (1H, d, J=8.7 Hz), 7.26–7.36 (3H, m), 7.41–7.44 (2H, m), 7.57 (1H, d, J=8.7 Hz).

Step 2: 8-Benzylthio-3-methyl-5-(pyridin-2-yl)-1,2,3,4-tetrahydronaphthalen-1-one In the same way as described in Example 1, using 8-benzylthio-5-bromo-3-methyl-1,2,3,4-tetrahydronaphthalen-1-one, the title compound (55 mg, 28%) was isolated as a yellow solid. mp 163–165° C. $C_{23}H_{21}NOS$ requires: C, 76.85; H, 5.89; N, 3.90%. Found: C, 76.73; H, 5.95; N, 3.72%. $^1$H NMR (360 MHz, CDCl$_3$), δ 1.04 (3H, d, J=6.5 Hz), 2.10–2.26 (1H, m), 2.32–2.40 (1H, m), 2.65–2.80 (2H, m), 2.92–2.97 (1H, m), 4.14 (1H, d, J=13 Hz), 4.18 (1H, d, J=13 Hz), 7.25–7.38 (4H, m), 7.44–7.46 (3H, m), 7.76 (1H, d of t, J=7.7 and 1.8 Hz), 8.68–8.72 (1H, m). MS (ES$^+$) 360 (M+1).

EXAMPLE 9
3-Methyl-8-(1-methyl-1,2,4-triazol-3-yl)methylthio-5-(thiazol-2-yl)-1,2,3,4-tetrahydronaphthalen-1-one In the same way as described in Intermediate 2, using Intermediate 3 and 3-chloromethyl-1-methyl-1,2,4-triazole, the title compound (60 mg, 56%) was isolated as a colourless solid. mp 130–131° C. $C_{18}H_{18}N_4OS_2.0.1$ ($H_2O$) requires: C, 58.07; H, 4.93; N, 15.05%. Found: C, 58.28; H, 4.85; N, 14.68%. $^1$H NMR (360 MHz, CDCl$_3$) δ 1.10 (3H, d, J=6.5 Hz), 2.16–2.29 (1H, m), 2.32–2.40 (1H, m), 2.73–2.84 (2H, m), 3.32–3.38 (1H, m), 3.88 (3H, s), 4.23 (2H, s), 7.43 (1H, d, J=3.4 Hz), 7.58 (1H, d, J=8.5 Hz), 7.69 (1H, d, J=8.5 Hz), 7.92 (1H, d, J=3.4 Hz), 7.95 (1H, s). MS (ES$^+$) 371 (M+1).

EXAMPLE 10
3,3-Dimethyl-8-methylthio-5-(pyridin-2-yl)-1,2,3,4-tetrahydronaphthalen-1-one
Step 1: 5-Bromo-3,3-dimethyl-8-methylthio-1,2,3,4-tetrahydronaphthalen-1-one In the same way as described in Intermediate 2, using Intermediate 4 and methyl iodide, the title compound (168 mg, 100%) was isolated as an orange gum. $^1$H NMR (360 Hz, CDCl$_3$) δ 1.09 (6H, s), 2.40 (3H, s), 2.53 (2H, s), 2.91 (2H, s), 7.04 (1H, d, J=8.7 Hz), 7.64 (1H, d, J=8.7 Hz). MS (ES$^+$) 299/301 ((M+1).

Step 2: 3,3-Dimethyl-8-methylthio-5-(pyridin-2-yl)-1,2,3,4-tetrahydronaphthalen-1-one In the same way as described in Example 1, using 5-bromo-3,3-dimethyl-8-methylthio-1,2,3,4-tetrahydronaphthalen-1-one, the title compound (105 mg, 63%) was isolated as a pale yellow solid. mp 152–154° C. $C_{18}H_{19}NOS.0.8$ ($H_2O$) requires: C, 69.33; H, 6.66; N, 4.49%. Found: C, 69.34; H, 6.28; N, 4.28%. $^1$H NMR (360 Hz, CDCl$_3$) δ 0.99 (6H, s), 2.45 (3H, s), 2.56 (2H, s), 2.85 (2H, s), 7.25–7.31 (2H, m), 7.37 (1H, d, J=7.8 Hz), 7.51 (1H, d, J=8.4 Hz), 7.79 (1H, d of t, J=7.6 and 1.8 Hz), 8.70–8.75 (1H, m). MS (ES$^+$) 298 (M+1).

The following Examples can also be made by the methodology disclosed herein and, together with their pharmaceutically acceptable salts, constitute part of the present invention:

(a) 3-Methyl-8-methylthio-5-(pyridin-2-yl)-1,2,3,4-tetrahydronaphthalen-1-one (b) 8-(Imidazol-3-yl)methylthio-3-methyl-5-(thiazol-2-yl)-1,2,3,4-tetrahydronaphthalen-1-one (c) 3-Methyl-8-(5-methylisoxazol-3-yl)methylthio-5-(thiazol-2-yl)-1,2,3,4-tetrahydronaphthalen-1-one (d) 3-Methyl-8-(2-hydroxyethyl)thio-5-(pyridin-2-yl)-1,2,3,4-tetrahydronaphthalen-1-one (e) 3-Methyl-5-(pyridin-2-yl)-8-(thien-2-yl)thio-1,2,3,4-tetrahydronaphthalen-1-one (f) 3-Methyl-8-(2-methylthiazol-4-yl)methylthio-5-(pyridin-2-yl)-1,2,3,4-tetrahydronaphthalen-1-one (g) 3-Methyl-8-(2-methylfur-3-yl)thio-5-(pyridin-2-yl)-1,2,3,4-tetrahydronaphthalen-1-one (h) 3-Methyl-8-phenylthio-5-(pyridin-2-yl)-1,2,3,4-tetrahydronaphthalen-1-one (i) (+)-3-Methyl-8-ethylthio-5-(pyridin-2-yl)-1,2,3,4-tetrahydronaphthalen-1-one (j) (−)-3-Methyl-8-ethylthio-5-(pyridin-2-yl)-1,2,3,4-tetrahydronaphthalen-1-one (k) 8-(2-Aminothiazol-4-yl)methylthio-3-methyl-5-(thiazol-2-yl)-1,2,3,4-tetrahydronaphthalen-1-one (l) 3-Methyl-5-(thiazol-2-yl)-8-(1,2,3-triazol-4-yl)methylthio-1,2,3,4-tetrahydronaphthalen-1-one (m) 8-(5-Methoxy-1,2,4-thiadiazol-3-yl)methylthio-3-methyl-5-(thiazol-2-yl)-1,2,3,4-tetrahydronaphthalen-1-one (n) 3-Methyl-5-(thiazol-2-yl)-8-(1,2,4-triazol-3-yl)methylthio-1,2,3,4-tetrahydronaphthalen-1-one (o) 3-Methyl-5-(pyridin-2-yl)-8-(pyridin-2-yl)methylthio-1,2,3,4-tetrahydronaphthalen-1-one (p) 3-Methyl-5-(thiazol-2-yl)-8-(thiazol-4-yl)methylthio-1,2,3,4-tetrahydronaphthalen-1-one (q) 8-Ethylthio-5-(2-methoxypyridin-6-yl)-3-methyl-1,2,3,4-tetrahydronaphthalen-1-one (r) 3-Methyl-5-(pyridin-2-yl)-8-(2,2,2-trifluoroethylthio)-1,2,3,4-tetrahydronaphthalen-1-one (s) 8-(5-Chloro-1,2,3-thiadiazol-4-yl)methylthio-3-methyl-5-(thiazol-2-yl)-1,2,3,4-tetrahydronaphthalen-1-one (t) 8-Ethylthio-5-(2-hydroxypyridin-6-yl)-3-methyl-1,2,3,4-tetrahydronaphthalen-1-one (u) 3-Methyl-8-methylthio-5-(thiazol-2-yl)-1,2,3,4-tetrahydronaphthalen-1-one (v) 8-Benzyloxy-3-methyl-5-(pyridin-2-yl)-1,2,3,4-tetrahydronaphthalen-1-one (w) 8-Ethylthio-5-(thiazol-2-yl)-1,2,3,4-tetrahydronaphthalen-1-one (x) 3-Methyl-8-(1-methylimidazol-2-yl)methylthio-5-(thiazol-2-yl)-1,2,3,4-tetrahydronaphthalen-1-one (y) 8-Isopropylamino-3-methyl-5-(pyridin-2-yl)-1,2,3,4-tetrahydronaphthalen-1-one (z) 8-Ethylthio-5-(pyridin-2-yl)-1,2,3,4-tetrahydronaphthalen-1-one (aa) 3-Methyl-8-(1-methyltetrazol-5-yl)methylthio-5-(thiazol-2-yl)-1,2,3,4-tetrahydronaphthalen-1-one (bb) 3-Methyl-8-propylamino-5-(pyridin-2-yl)-1,2,3,4-tetrahydronaphthalen-1-one (cc) 3-Methyl-8-(1-methyl-1,2,4-triazol-5-yl)methylthio-5-(pyridin-2-yl)-1,2,3,4-tetrahydronaphthalen-1-one (dd) 8-(Imidazol-2-yl)methylthio-3-methyl-5-(thiazol-2-yl)-1,2,3,4-tetrahydronaphthalen-1-one (ee) 8-Ethyl-3-methyl-5-(pyridin-2-yl)-1,2,3,4-tetrahydronaphthalen-1-one (ff) 8-Ethylthio-3-methyl-5-(thien-2-yl)-1,2,3,4-tetrahydronaphthalen-1-one.

(gg) 3,3-Dimethyl-8-(1-methyl-1,2,4-triazol-3-yl)methylthio-5-(thiazol-2-yl)-1,2,3,4-tetrahydronaphthalen-1-one.

(hh) 3,3-Dimethyl-8-(1,2,3-triazol-4-yl)methylthio-5-(thiazol-2-yl)-1,2,3,4-tetrahydronaphthalen-1-one.

(ii) 3,3-Dimethyl-2-hydroxyethylthio-5-(thiazol-2-yl)-1,2,3,4-tetrahydronaphthalen-1-one.

(jj) 3,3-Dimethyl-8-(pyridin-4-yl)methylthio-5-(thiazol-2-yl)-1,2,3,4-tetrahydronaphthalen-1-one.

(kk) 3,3-Dimethyl-8-(imidazol-3-yl)methylthio-5-(thiazol-2-yl)-1,2,3,4-tetrahydronaphthalen-1-one.

(ll) 3,3-Dimethyl-8-(pyridin-3-yl)methylthio-5-(thiazol-2-yl)-1,2,3,4-tetrahydronaphthalen-1-one.

(mm) 3,3-Dimethyl-8-(pyridin-2-yl)methylthio-5-(thiazol-2-yl)-1,2,3,4-tetrahydronaphthalen-1-one.

(nn) 8-(2-Methoxyethylthio)-3,3-dimethyl-5-(thiazol-2-yl)-1,2,3,4-tetrahydronaphthalen-1-one.

(oo) 3-(6,6-Dimethyl-8-oxo-4-(thiazol-2-yl)-5,6,7,8-tetrahydronaphthalen-1-ylthio)propionamide.

(pp) 3,3-Dimethyl-8-benzylthio-5-(thiazol-2-yl)-1,2,3,4-tetrahydronaphthalen-1-one.

(qq) 3,3-Dimethyl-8-(3-dimethylamino)propylthio-5-(thiazol-2-yl)-1,2,3,4-tetrahydronaphthalen-1-one.

(rr) 8-(2-Dimethylamino)ethylthio-3-methyl-5-(thiazol-2-yl)-1,2,3,4-tetrahydronaphthalen-1-one.

(ss) N,N-Dimethyl-2-(6-methyl-8-oxo-4-(thiazol-2-yl)-5,6,7,8-tetrahydronaphthalen-1-ylthio)acetamide.

(tt) 7-Ethylthio-4-(pyridin-2-yl)indan-1-one.

(uu) 8-(3-Aminopropyl)thio-3,3-dimethyl-5-(thiazol-2-yl)-1,2,3,4-tetrahydronaphthalen-1-one.

(vv) 5-[(6,6-Dimethyl-8-oxo-4-(thiazol-2-yl)-5,6,7,8-tetrahydronaphthalen-1-yl)thiomethyl]oxazolidin-2-one.

(ww) 3-Methyl-5-(1-oxypyridin-2-yl)-8-phenylthio-1,2,3,4-tetrahydronaphthalen-1-one.

(xx) 3-Methyl-5-(1-oxypyridin-2-yl)-8-(thien-2-ylthio)-1,2,3,4-tetrahydronaphthalen-1-one.

(yy) 3-Methyl-8-(2-methylfuran-3-yl)thio-5-(1-oxypyridin-2-yl)-1,2,3,4-tetrahydronaphthalen-1-one.

(zz) 3-Methyl-8-ethylthio-5-(1-oxypyridin-2-yl)-1,2,3,4-tetrahydronaphthalen-1-one.

(aaa) Trifluoromethanesulphonic acid 6-methyl-8-oxo-4-(thiazol-2-yl)-5,6,7,8-tetrahydronaphthalen-1-yl ester.

(bbb) Thiophene-2-sulphonic acid 6-methyl-8-oxo-4-(thiazol-2-yl)-5,6,7,8-tetrahydronaphthalen-1-yl ester.

(ccc) 4-Methylbenzenesulphonic acid 6-methyl-8-oxo-4-(thiazol-2-yl)-5,6,7,8-tetrahydronaphthalen-1-yl ester.

EXAMPLE 11

3-Methyl-5-(1-oxypyridin-2-yl)-8-phenylthio-1,2,3,4-tetrahydronaphthalen-1-one

Step 1: 3-Methyl-8-methylsulphonyl-5-(1-oxypyridin-2-yl)-1,2,3,4-tetrahydronaphthalen-1-one To a solution of 3-methyl-8-methylthio-5-(pyridin-2-yl)-1,2,3,4-tetrahydronaphthalen-1-one (1.0 g, 3.5mmol) in DCM (100 mL) and dioxan (25 mL) was added m-chloroperoxybenzoic acid (70%, 10.6 mmol, 2.61 g). The mixture was stirred at room temperature for 4 h. The mixture was poured into $NaHCO_3$ (sat., 75 mL) and the two phases separated. The organic phase was washed with further $NaHCO_3$ (sat., 75 mL), dried ($Na_2SO_4$) and evaporated. The residue was chromatographed on silica gel, eluting with EtOAc:hexane (1:1–100:0), to afford the title compound (1.03 g, 88%) as a cream solid. mp 145–148° C. $C_{17}H_{17}NO_4S.0.9(H_2O)$ requires: C,58.74; H,5.45; N,4.03%. Found: C,58.86; H,5.09; N,3.86%. $^1$H NMR (360 MHz, $CDCl_3$) δ 1.08 (3H,d, J=6.3 Hz), 2.10–2.36 (1H,m), 2.41–2.56 (2H,m), 2.84–3.01 (2H,m), 3.59 (3H,S), 7.30–7.44(3H,m), 7.57 (1H,d, J=8.1 Hz), 8.27 (1H,d, J=8.0 Hz), 8.36–8.40(1H,m). MS (ES$^+$) 332 (M+1).

Step 2: 3-Methyl-5-(1-oxypyridin-2-yl)-8-phenylthio-1,2,3,4-tetrahydronaphthalen-1-one To a solution of the sulphone (0.1 g, 0.30 mmol) in THF (10 mL) at 0° C. was added thiophenol sodium salt (40 mg, 0.30 mmol). This mixture was stirred for 1.5 h. Further thiophenol sodium salt (20 mg, 0.15 mmol) was added and the mixture stirred for a further 1 h. Water (20 mL) and EtOAc (20 mL) were added and the organic phase separated, dried ($Na_2SO_4$) and evaporated. The residue was chromatographed on silica gel eluting with DCM:MeOH (95:5) to afford a pale yellow foam. After trituration with ether, the title compound (78 mg, 72%) was isolated as a pale yellow solid. mp 129–132° C. $C_{22}H_{19}NO_2S.O.2(H_2O)$ requires: C,72.38; H,5.36; N, 3.84%. Found: C,72.39; H,5.44; N,4.01%. $^1$H NMR (360 MHz, $CDCl_3$) δ 1.05–1.09(3H,m), 2.16–2.54(3H,m), 2.79–3.08 (2H,m), 6.69–6.74(1H,m), 7.05–7.12(1H,m), 7.26–7.32(3H,m), 7.44–7.46(3H,m), 7.60–7.64(2H,m), 8.32–8.36(1H,m). MS (ES$^+$) 362 (M+1).

EXAMPLE 12

3-Methyl-5-(1-oxypyridin-2-yl)-8-(thien-2-ylthio)-1,2,3,4-tetrahydronaphthalen-1-one To a suspension of NaH (60%, 15 mg, 0.36 mmol) in THF (10 mL) was added thiophene-2-thiol (34 μl, 0.36 mmol). This mixture was stirred at room temperature for 10 min and then 3-methyl-8-methylsulphonyl-5-(1-oxypyridin-2-yl)-1,2,3,4-tetrahydronaphthalen-1-one (0.1 g, 0.30 mmol) was added. This mixture was stirred at room temperature for 1 h after which time the mixture was partitioned between EtOAc (2×25 mL) and water (25 mL). The combined organic phases were dried (Na$_2$SO$_4$) and evaporated and the residue was chromatographed on silica gel, eluting with DCM:MeOH (95:5) to afford a pale yellow gum. After trituration with ether:hexane (1:1), the title compound (10 mg, 9%) was isolated as a cream solid. mp 125° C. (dec.). C$_{20}$H$_{17}$NO$_2$S$_2$.0.125(H$_2$O) requires: C,64.97; H,4.70; N,3.79%. Found: C,64.57; H,4.30; N,3.44%. $^1$HNMR (360 MHz, CDCl$_3$) δ 1.04–1.09(3H,m), 2.14–2.52(3H,m), 2.78–3.03(2H,m), 6.82–6.87(1H,m), 7.14–7.33(6H,m), 7.57–7.60(1H,m), 8.30–8.36(1H,m). MS(ES$^+$) 368(M+1).

EXAMPLE 13

3-Methyl-8-(2-methylfuran-3-yl)thio)-5-(1-oxypyridin-2-yl)-1,2,3,4-tetrahydronaphthalen-1-one In the same way as described in Example 12, using 2-methyl-3-furanthiol, the title compound was isolated (40 mg, 36%) as a yellow solid. mp 125° C. (dec.). C$_{21}$H$_{19}$NO$_2$S.0.5(H$_2$O) requires: C,67.36; H,5.38; N,3.74%. Found: C,67.41; H,5.06; N,3.63%, $^1$H NMR (360 MHz, CDCl$_3$) δ 1.05–1.08(3H,m), 2.16–2.52(6H,m), 2.77–3.08 (2H,m), 6.36–6.37(1H,m), 6.93–6.98(1H,m), 7.14–7.21(1H, m), 7.25–7.36(3H,m) 7.42–7.44(1H,m), 8.32–8.38(1H,m). MS(ES$^+$) 366(M+1).

EXAMPLE 14

3-Methyl-8-ethylthio-5-(1-oxypyridin-2-yl)-1,2,3,4-tetrahydronaphthalen-one

In the same way as described in Example 11, using ethanethiol sodium salt, the title compound was isolated (54 mg, 57%) as a pale yellow solid. mp 106–110° C. C$_{18}$H$_{19}$NO$_2$S.0.2(H$_2$O) requires: C,68.20; H,6.17; N,4.42%. Found: C,68.26; H,6.04; N,4.32%. $^1$H NMR (360 MHz, CDCl$_3$) δ 1.02–1.06(3H,m), 1.42 (3H,t, J=7.4 Hz), 2.12–2.50(3H,m), 2.72–3.04(4H,m), 7.26–7.35(5H,m), 8.32–8.38(1H,m). MS(ES$^+$) 314(M+1).

EXAMPLE 15

Trifluoromethanesulphonic acid 6-methyl-8-oxo-4-(thiazol-2-yl)-5,6,7,8-tetrahydronaphthalen-1-yl ester To a cooled solution of 8-hydroxy-3-methyl-5-(thiazol-2-yl)-1,2,3,4-tetrahydronaphthalen-1-one (Intermediate 3, Step 1) (0.42 g, 1.61 mmol) and pyridine (0.31 mL, 3.9 mmol) in DCM (30 mL) at −78° C. was added trifluoromethanesulphonic anhydride (0.47 mL, 2.9 mmol). This mixture was warmed to room temperature and stirred for 2.5 h. Further trifluoromethanesulphonic anhydride (0.47 mL, 2.9 mmol) and pyridine (0.31 mL, 3.9 mmol) was added and the mixture stirred for another 4 h. The solution was poured into NaHCO$_3$ (sat., 50 mL) and the two phases separated. The aqueous phase was extracted with DCM (50 mL) and the combined organics dried (Na$_2$SO$_4$) and evaporated. The residue was chromatographed on silica gel, eluting with EtOAc:hexane (20:8–50:50), to afford the title compound (0.19 g, 30%) as a yellow foam. C$_{15}$H$_{12}$NO$_4$S$_2$F$_3$ requires: C,46.03; H,3.09; N,3.58. Found: C,46.48; H,2.85; N,3.40%. $^1$H NMR (360 MHz, CDCl$_3$) δ 1.14(3H,d, J=6.5 Hz), 2.24–2.36(1H,m), 2.43(1H,dd, J=12.3, 16.1 Hz), 2.77–2.89 (2H,m), 3.30–3.37(1H,m), 7.24(1H,d,8.5 Hz), 7.52(1H,d, J=3.3 Hz), 7.84(1H,d, J=8.5 Hz), 7.99(1H,d, J=3.4 Hz). MS(ES$^+$) 392 (M+1).

EXAMPLE 16

Thiophene-2-sulphonic acid 6-methyl-8-oxo-4-(thiazol-2-yl)-5,6,7,8-tetrahydronaphthalen-1-yl ester Step 1: Thiophene-2-sulphonic acid 4-bromo-6-methyl-8-oxo-5,6,7,8-tetrahydronaphthalen-1-yl ester To a solution of 5-bromo-8-hydroxy-3-methyl-1,2,3,4-tetrahydronaphthalen-1-one (Intermediate 1, Step 1) (0.2 g, 0.78 mmol) in DCM (10 mL) was added Et$_3$N (1.1 mL, 7.8 mmol) and thiophene-2-sulphonyl chloride (0.57 g, 3.1 mmol). This mixture was stirred at room temperature for 5 h, and then partitioned with DCM (20 mL) and water (20 mL). The two phases were separated and the aqueous phase extracted with DCM (20 mL). The combined organic phases were dried (Na$_2$SO$_4$) and evaporated. The residue was chromatographed on silica gel eluting with EtOAc:hexane (10:90–35:65) to afford the title compound (0.24 g, 75%) as an orange solid. mp 110–113° C. $^1$H NMR (360 MHz, CDCl$_3$) δ 1.14(3H,d, J=6.0 Hz), 2.10–2.30(2H,m), 2.48–2.62(2H,m) 3.16–3.22(1H,m), 7.02(1H,d, J=8.7 Hz), 7.14(1H,dd, J=3.8, 4.9 Hz), 7.69–7.76(3H,m). MS(ES$^+$) 401/403 (M+1).

Step 2: Thiophene-2-sulphonic acid 6-methyl-8-oxo-4-(thiazol-2-yl)-5,6,7,8-tetrahydronaphthalen-1-yl ester In the same way as described in Intermediate 3, Step 1, using thiophene-2-sulphonic acid 4-bromo-6-methyl-8-oxo-5,6,7,8-tetrahydronaphthalen-1-yl ester, the title compound (50 mg, 50%) was isolated as a cream solid. mp 111–113° C. C$_{18}$H$_{15}$NO$_4$S$_3$ requires: C,53.31; H,3.73; N,3.45%. Found: C,53.50; H,3.62; N,3.64%. $^1$H NMR (360 MHz, CDCl$_3$) δ 1.08 (3H,d, J=6.4 Hz), 2.14–2.32 (2H,m), 2.59–2.65 (1H,m), 2.76 (1H,dd, J=10.3, 17.5 Hz), 3.22–3.32(1H,m), 7.14(1H, dd, J=3.8, 5.0 Hz). 7.23(1H,d, J=8.4 Hz). 7.49 (1H,d, J=3.2 Hz), 7.72–7.78(3H,m), 7.96(1H,d, J=3.3 Hz). MS (ES$^+$) 406 (M+1).

What is claimed is:

1. A compound of formula (I) or a pharmaceutically acceptable salt thereof:

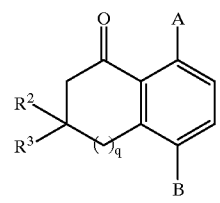

(I)

where A is C$_{1-6}$alkyl, C$_{2-6}$alkenyl, C$_{2-6}$alkynyl, C$_{3-6}$cycloalkyl, arylC$_{1-6}$alkyl, aryl, S(O)$_p$(CH$_2$)$_n$R$^1$, OR$^1$, NR$^1$R$^{12}$ or OS(O)$_r$R$^1$;

B is a 6-membered aromatic ring containing 1 nitrogen atom, which ring is optionally substituted by one or more substituents independently chosen from: C$_{1-6}$alkyl; C$_{1-6}$haloalkyl; C$_{1-6}$alkoxy; hydroxy; halogen; S(O)$_r$R$^4$; COR$^5$; and aryl or arylC$_{1-6}$alkyl wherein the aryl ring is optionally substituted by one, two or three substituents independently chosen from halogen, CF$_3$, OCH$_3$, nitro and cyano; and the N atom of the 6-membered aromatic ring is optionally substituted by an O atom;

$R^1$ is hydrogen; $C_{1-6}$alkyl, $C_{2-6}$alkenyl, $C_{2-6}$alkynyl, $C_{3-6}$cycloalkyl, or $C_{3-6}$cycloalkenyl each of which is optionally substituted by amino, aminocarbonyl, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen which ring is optionally substituted by $C_{1-6}$alkyl on the further nitrogen atom or by an oxo group on a carbon atom; aryl, aryl$C_{1-6}$alkyl, aryl$C_{1-6}$alkenyl or aryl$C_{2-6}$alkynyl optionally substituted on the aryl ring by $C_{1-6}$alkyl, halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ is $NR^6R^7$, $C_{1-6}$alkyl, $C_{2-8}$alkenyl, $C_{2-8}$alkynyl, aryl or $CH_2(CO)_mNR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl, aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl, $C_{2-6}$alkenyl, $C_{2-6}$alkynyl; or phenyl optionally substituted by one, two or three substituents independently chosen from halogen, $CF_3$, $OCH_3$, nitro and cyano;

$R^{12}$ is hydrogen or $C_{1-6}$alkyl;

l is zero, 1 or 2;

m is zero or 1;

n is 0, 1 or 2;

p is zero, 1 or 2;

q is 0, 1 or 2; and r is 0, 1 or 2.

2. A compound according to claim 1 wherein A is $S(O)_p(CH_2)_nR^1$, $OR^1$ or $OS(O)_rR^1$.

3. A compound according to claim 1 wherein:

A is, $S(O)_p(CH_2)_nR^1$, $OS(O)_lR^1$; $OR^1$, $NR^1R^{12}$ or $C_{1-6}$alkyl;

B is a pyridine which is unsubstituted or substituted by $C_{1-6}$alkyl; $C_{1-6}$alkoxy; hydroxy or halogen;

$R^1$ is $C_{1-6}$alkyl optionally substituted by one, two or three fluorine atoms; phenyl optionally substituted by chlorine, fluorine or methoxy; or pyridine, isoxazole, tetrazole, thiophene, furan, thiazole, imidazole, triazole or thiadizole each of which is unsubstituted or substituted by $C_{1-6}$alkyl or chlorine;

$R^2$ and $R^3$ are independently hydrogen or methyl;

l is 2;

m is zero or 1;

n is zero or 1;

p is zero, 1 or 2;

q is 1; and r is 1.

4. A pharmaceutical composition comprising an effective amount of a compound according to claim or a pharmaceutically acceptable salt thereof and a pharmaceutically acceptable excipient.

5. A method of treatment of a condition which requires the administration of a cognition enhancing agent which comprises administering to a subject suffering from or prone to such a condition a therapeutically effective amount of a compound according to claim 1 or a pharmaceutically acceptable salt thereof.

* * * * *